United States Patent [19]

Wu

[11] Patent Number: 4,611,580
[45] Date of Patent: Sep. 16, 1986

[54] INTERVERTEBRAL BODY STABILIZATION

[75] Inventor: Kent K. Wu, Royal Oak, Mich.

[73] Assignee: Henry Ford Hospital, Detroit, Mich.

[21] Appl. No.: 555,363

[22] Filed: Nov. 23, 1983

[51] Int. Cl.⁴ .............................................. A61F 5/04
[52] U.S. Cl. .................................... 128/69; 128/92 B; 128/92 A
[58] Field of Search ................... 128/69, 92 A, 92 R, 128/92 BB, 92 B

[56] References Cited

U.S. PATENT DOCUMENTS

| 3,842,825 | 10/1974 | Wagner | 128/92 BB |
| 4,041,939 | 8/1977 | Hall | 128/69 |
| 4,274,401 | 6/1981 | Miskew | 128/69 |
| 4,433,677 | 2/1984 | Ulrich et al. | 128/69 |
| 4,445,513 | 5/1984 | Ulrich et al. | 128/69 |

Primary Examiner—Gene Mancene
Assistant Examiner—C. W. Shedd
Attorney, Agent, or Firm—Barnes, Kisselle, Raisch, Choate, Whittemore & Hulbert

[57] ABSTRACT

A method and apparatus for stabilizing the spine wherein a bone graft has been provided between oppositely spaced vertebral bodies in the space where vertebral bodies have been removed which comprises forming spaced transversely extending holes in the vertebral bodies, and applying a stabilizing device. The stabilizing device comprises screws that are threaded into the holes and a threaded shaft that is attached and fixed with respect to the screws, to stabilize the vertebral bodies.

4 Claims, 3 Drawing Figures

INTERVERTEBRAL BODY STABILIZATION

This invention relates to the stabilization of a spine wherein vertebral body portions of the spine have been removed and bone grafts have been provided to replace the removed vertebral body portions.

Background and Summary of the Invention

In the treatment of diseases or injuries to the spine, it has been common to utilize bone grafts, known as bone fusion, to take the place of portions of the spine that have been removed. Bone fusion is effective to provide support but it requires a slow and prolonged recovery.

Among the objectives of the present invention are to provide a method and apparatus for stabilizing the spine wherein bone fusion has been used that permits the patient to move about more readily and promptly as the bone graft continues to heal.

In accordance with the invention, the method and apparatus of stabilizing the spine wherein a bone graft has been provided between oppositely spaced vertebral bodies in the space where vertebral bodies have been removed comprises forming spaced transversely extending holes in the vertebral bodies, utilizing a stabilizing device comprising screws that are threaded into the holes and rigid attaching means are locked between the screws to stabilize the vertebral bodies.

Description

Figure 1:
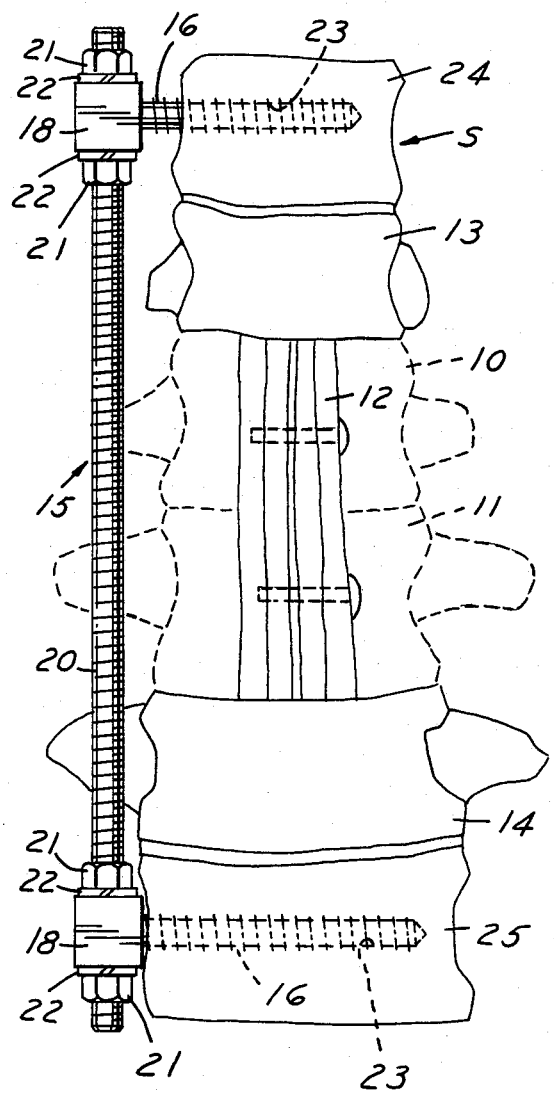
FIG. 1 is a front elevational view showing a spine in which a stabilizing device embodying the invention has been placed.
Figure 2:
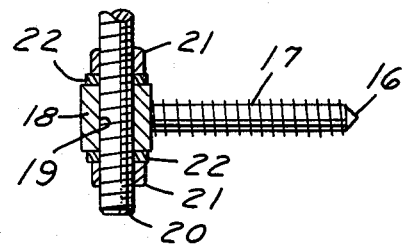
FIG. 2 is a fragmentary sectional view of the stabilizing device.
Figure 3:
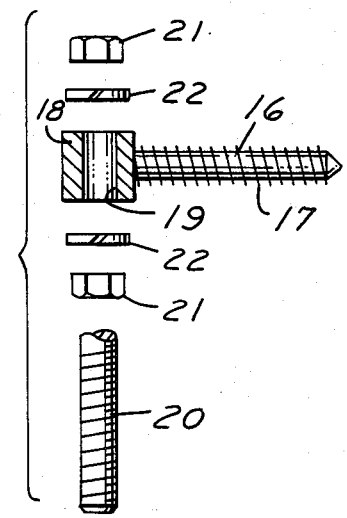
FIG. 3 is a fragmentary exploded view of the stabilizing device.

Referring to FIGS. 1-3, there is shown a spine S wherein vertebral body portions 10, 11 shown by broken lines, have been removed and bone fusion 12 has been provided between the remaining and opposed vertebral bodies 13, 14.

In order to provide immediate stabilization to the spine and the patient can move during the healing, a stabilizer device 15 is utilized that comprises spaced screws 16 that preferably have a thread 17 with a course thread commonly called a cancellous thread. Each screw 16 includes a block or head 18 having a transverse opening 19 that is large enough to receive a shaft 20 so that the screw 16 can be readily moved along the shaft. The shaft 20 is threaded and nuts 21 are threaded on opposite sides of each head or block to lock each screw in longitudinally spaced position on the shaft. Lock washers 22 are interposed between each nut 21 and the block 18.

In accordance with the method, transverse holes 23 are provided in the vertebral bodies 24, 25 that are adjacent the vertebral bodies 13, 14 between which the bone fusion has been provided. The holes 23 are accurately formed parallel to one another preferably by a method and apparatus as shown in my copending application Ser. No. 521,682 filed Aug. 10, 1983, incorporated herein by reference.

Each screw 16 is then threaded into a hole 23 and the shaft 20 is passed through the openings 19 in the heads 18 of the respective screws 16 and the nuts are tightened to provide the desired vertical distance between the vertebral bodies.

In order to be able to thread the nuts 21 on threaded shaft 20, the shaft 20 is first inserted through the opening 19 in one block 18 and two nuts 21 and associated lock washers 22 are threaded on the end of the threaded shaft 20 that has been inserted. The nuts are then threaded toward the middle of the threaded shaft 20 to permit the end of the shaft 20 to be inserted in the opening 19 of the block 18 of the other screw 16. The two nuts 21 can then be threaded outwardly toward the respective ends and the additional nuts 21 and lock washers 22 applied.

The holes 23 which receive the screws 16 extends substantially through the vertebral bodies 24, 25 but are spaced from the opposite side. Since the holes 23 are parallel, a strong and effective vertical load bearing capacity is provided such that the patient can move about promptly after the operation and during the healing of the bone fusion.

The stabilizer device can be left in the patient or alternatively removed after the bone fusion has healed depending upon the size and load that the bone fusion must withstand. If the patient is of such a size that some supplemental stabilization is required, the stabilizing device may be left in the patient.

I claim:

1. The method of stabilizing the spine wherein a bone graft has been provided between oppositely spaced vertebral bodies in the space where vertebral bodies have been removed which comprises forming spaced transversely extending parallel holes in one side of the oppositely spaced vertebral bodies, threading a screw fixedly attached to a head, having an unthreaded opening and opposed flattened sides at the ends of said opening, into each said hole;

bringing the unthreaded openings in said heads in alignment, passing a threaded shaft through the aligned unthreaded openings in said heads and threading opposed nuts into engagement with opposed flattened sides of each head until the desired distance between the opposed vertebral bodies is achieved, thereafter tightening said nuts in adjusted position engaging said opposed flattened sides to stabilize the vertebral bodies.

2. A vertebral body stabilizer for stabilizing the spine wherein a bone graft has been provided between oppositely spaced vertebral bodies comprising spaced laterally extending screws adapted to be threaded into the sides of the oppositely spaced bodies, each screw including a head fixed at one end having an unthreaded transverse opening and opposed flattened sides at the ends of said opening therethrough, a shaft slidably extending through said openings in said heads, said shaft being threaded, and means threaded on said shaft and engaging said opposed flattened sides of each said head for adjusting the desired distance between the opposed vertebral bodies and for locking said screws in adjusted positioned on said shaft in longitudinally spaced relation to one another.

3. The stabilizer set forth in claim 2 wherein said means for adjusting and locking said screws comprises opposed nuts adapted to engage the head of each said screw.

4. The stabilizer set forth in claim 3 including locking washers interposed between each nut and the associated head.

* * * * *